United States Patent
Hadley et al.

(10) Patent No.: US 10,015,372 B2
(45) Date of Patent: Jul. 3, 2018

(54) DE-GHOSTING OF IMAGES CAPTURED USING A CAPSULE CAMERA

(71) Applicant: CapsoVision, Inc, Saratoga, CA (US)

(72) Inventors: Mark Hadley, Los Altos, CA (US); Gordon C. Wilson, San Francisco, CA (US)

(73) Assignee: CAPSOVISION INC, Saratoga, CA (US)

( * ) Notice: Subject to any disclaimer, the term of this patent is extended or adjusted under 35 U.S.C. 154(b) by 143 days.

(21) Appl. No.: 15/335,301

(22) Filed: Oct. 26, 2016

(65) Prior Publication Data

US 2018/0115685 A1    Apr. 26, 2018

(51) Int. Cl.
| | |
|---|---|
| A62B 1/04 | (2006.01) |
| H04N 5/21 | (2006.01) |
| A61B 1/04 | (2006.01) |
| A61B 1/00 | (2006.01) |
| A61B 1/06 | (2006.01) |
| H04N 5/225 | (2006.01) |

(52) U.S. Cl.
CPC ......... *H04N 5/211* (2013.01); *A61B 1/00009* (2013.01); *A61B 1/041* (2013.01); *A61B 1/0661* (2013.01); *A61B 1/0684* (2013.01); *H04N 2005/2255* (2013.01)

(58) Field of Classification Search
CPC ............ H04N 5/211; H04N 2005/2255; A61B 1/0661; A61B 1/00009; A61B 1/0684; A61B 1/041
USPC .......................................................... 348/65
See application file for complete search history.

(56) References Cited

U.S. PATENT DOCUMENTS

| | | | |
|---|---|---|---|
| 8,405,711 B2 | 3/2013 | Wang et al. | |
| 8,636,653 B2 | 1/2014 | Wilson | |
| 2009/0306474 A1* | 12/2009 | Wilson | A61B 1/041 600/109 |
| 2011/0080401 A1* | 4/2011 | Tan | H04N 13/0018 345/419 |

* cited by examiner

*Primary Examiner* — Allen Wong
(74) *Attorney, Agent, or Firm* — Blairtech Solution LLC

(57) ABSTRACT

A method of reducing ghost in images captured using a capsule endoscope while travelling in the gastrointestinal (GI) tract. The captured images contain ghost caused by reflections of multiple light sources by capsule housing of the capsule endoscope. The method derive, from the plurality of images, a ghost model comprising multiple ghost coefficients for relating light energies from the multiple light sources for a given image with ghost signals at multiple pixel locations for the given image. De-ghosted images are generated by compensating the plurality of images using estimated ghost signals based on derived ghost coefficients and the light energies from the multiple light sources. The process of deriving, from the plurality of images, the ghost model comprises removing any sensor gamma or any other non-linearity in pixel values of the plurality of images associated with the light energy.

18 Claims, 5 Drawing Sheets

DE-GHOSTING OF IMAGES CAPTURED USING A CAPSULE CAMERA

CROSS REFERENCE TO RELATED APPLICATIONS

The present invention is related to U.S. Pat. No. 8,636,653, issued on Jan. 28, 2014 and U.S. Pat. No. 8,405,711, issued on Mar. 26, 2013. The U.S. patents are hereby incorporated by reference in their entireties.

FIELD OF THE INVENTION

The present invention relates to image processing for images captured with a capsule endoscope travelling through the gastrointestinal (GI) tract. In particular, the present invention discloses techniques to reduce ghosts caused by light reflection from the capsule housing.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools.

Capsule endoscope is an alternative in vivo endoscope developed in recent years. For capsule endoscope, a camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system was disclosed in the U.S. Pat. No. 8,636,653, entitled "In vivo camera with multiple sources to illuminate tissue at different distances" granted on Jan. 28, 2014. One embodiment disclosed in U.S. Pat. No. 8,636,653 uses multiple electromagnetic radiation sources to illuminate surface of an organ (e.g. the mucosa surface of intestines) so that images can be captured from the light that is scattered off of the surface. FIG. 1 illustrates an example of use of an endoscope having two light emitters, for illumination and imaging over short distances. Specifically as illustrated in FIG. 1 on the right side, mucosa surface 101 at points F and G which is close to (e.g. <5 mm) or touching endoscope 100, is illuminated by light emerging from a compound parabolic concentrator (CPC) 113, both directly and after reflection from reflector 118. In the illustrative embodiment shown in FIG. 1, reflector 118 enables light from an emitter in short-range source 103 to reach an illumination region of the endoscope from both sides of the field of view, thereby to illuminate tissue surface 101 more uniformly in an image to be diagnosed, as compared to short-range illumination from only one side of the field of view.

Additionally, a tissue surface 101 located at point H which is in contact with endoscope 100 is also illuminated by light emerging from surface 114 which light entered CPC 113 through a bottom surface as described above, and is reflected by a convex surface in CPC 1100. As tissue surface 101 is in contact with inside of endoscope housing 102, point H is outside the FOV of the camera. However, as the distance increases, point H falls within the FOV. Accordingly, endoscope 100 uses a minimum amount of energy, e.g. by using primarily just a single LED within short-range source 103 in the direction towards the right of FIG. 1.

Note that endoscope 100 of these embodiments includes an additional LED used for long-range sources (104, 107) that, when turned on, also provides light in the same radial direction, i.e. towards the right and left of FIG. 1. Long-range sources (104, 107) are positioned longitudinally offset from the objective's optical axis, e.g. positioned behind mirror 118 which acts as a baffle. Note that there is little or no overlap between the long-range illumination regions on the endoscope's tubular wall (close to point E in FIG. 1) lit up by light source 104, and the above-described short-range illumination region lit up by light source 103. The area of long-range illumination region lit up by light source 104 is several times and in some cases an order of magnitude, smaller than the corresponding area of short-range illumination region lit up by light source 103.

Endoscope 100 increases the radiant energy generated by the long-range light source 104 as the distance of the tissue to be imaged increases. Using long-range light source 104 simultaneously with short-range light source 101 provides sufficient illumination to image mucosa 101 that is located far away (e.g. ~20 mm away). For example, points A-D shown on the left side of FIG. 1 are illuminated by turning on both light sources 106 and 107.

Use of both light sources 106 and 107 does use up a maximum amount of energy (relative to use of just one source 106), although such use provides better images which enable a more thorough diagnosis of a body cavity, such as a gastrointestinal tract. The energy generated by multiple light sources 103 and 104 to illuminate radially in a given direction may be scaled appropriately, to illuminate tissue located at intermediate distance(s). Accordingly, endoscope 100 in some embodiments of the invention operates multi-modally, specifically in a minimum energy mode, a maximum energy mode and one or more intermediate energy modes. For certain body cavities, such as a small intestine, endoscope 100 of these embodiments operates continuously in a minimal mode, by turning on only the short-range source, e.g. source 103 (i.e. the long-range source is kept turned off).

Note that endoscope 100 of FIG. 1 incorporates four objectives with optical axes spaced 90° apart, although only two lenses 111 and 112 that are oppositely directed are shown in FIG. 1. In this example, eight LEDs are arrayed in a ring under an annular truncated CPC 113. The eight LEDs emit out the outer surface 114 of CPC 113 and also through the top of the CPC apertures A2 (not labeled in FIG. 1). Some of the light from aperture A2 is reflected down and out of the endoscope 100 by annular mirror 118 located above the imaging region. In FIG. 1, the angle of the mirror 118 relative to the optical axis is chosen such that the reflected light satisfies the relationship $\theta_r < \theta_2$ where $\theta_2$ is the maximum angle of light exiting the CPC cavity in the radial direction and $\theta_r$ is the angle of a ray reflected from the annular mirror relative to an inner or outer surface of the tubular wall.

The sensor, sources and optical elements in the capsule endoscope are properly arranged to avoid overlaps between long-range illumination region and imaging region as well as between short-range illumination region and imaging region so as to eliminate or reduce any possibility that a virtual image (also called "ghost"), due to long-range light or the short-range light reflected by housing 102, is present in an image that is captured by the camera and used for diagnosis. The ghost-forming light passes from the source to the housing directly or indirectly, in the latter case first scattering off objects within the capsule housing. Also, the housing has a transparent region (window) and image-forming rays enter the housing at the same location in the transparent region from which ghost-forming light reflects/ scatters. A ghost forming ray is collinear with an image-forming ray originating outside the capsule. Image forming rays are formed by light from objects outside the housing illuminated by the light source. In practice, the proper arrangement of sources and optical elements in the capsule endoscope has helped to substantially reduce the ghosts. Nevertheless, certain degrees of ghosts are still visible in the captured images. The ghosts typically occur when light from short-range sources scatters off of surfaces inside the capsule housing and then reflects from the housing into a camera objective. In order to eliminate a ghost from reflection of long-range light or short-range light by the housing, one solution is to have the sensor operated to exclude the ghost e.g. by cropping the image. During cropping, only a part of an image in a central region thereof is transmitted by endoscope 100 to a computer for use in diagnosis by excluding the rest of the image containing the ghost. Alternatively, the full-size images can be transmitted to the computer and the cropping can be done by the computer. While this method is simple, some imaging areas have to be sacrificed.

Accordingly it is desirable to develop techniques to eliminate ghosts without the need for sacrificing valuable imaging areas.

BRIEF SUMMARY OF THE INVENTION

A method of reducing ghost in images captured using a capsule endoscope while travelling in the gastrointestinal (GI) tract. The captured images contain ghosts caused by reflections of multiple light sources by capsule housing of the capsule endoscope. The method derives, from the plurality of images, a ghost model comprising multiple ghost coefficients for relating light energies from the multiple light sources for a given image with ghost signals at multiple pixel locations for the given image. De-ghosted images are generated by compensating the plurality of images using estimated ghost signals based on derived ghost coefficients and the light energies from the multiple light sources. The process of deriving, from the plurality of images, the ghost model comprises removing any sensor gamma or any other non-linearity in pixel values of the plurality of images associated with the light energy. Each captured image is modelled as a sum of first pixel values corresponding to true pixel values and ghost signals at respective pixel locations within each picture. The true pixel value at a given pixel location is estimated by a sum of weighted first pixel values at neighboring locations of the given pixel location to derive an estimated true pixel value. For example, the true pixel value at the given pixel location is estimated by an average of the first pixel values at neighboring locations of the given pixel location.

The ghost coefficients at the given pixel location can be estimated by minimizing errors between estimated pixel values and true pixel values calculated over multiple frames. The errors between estimated pixel values and true pixel values may correspond to mean squared errors. In one embodiment, the ghost coefficients are allowed to be non-negative only and a non-negative least squares process is used to derive the ghost coefficients. An iterative design procedure is also disclosed, where the ghost coefficients are initially set to all zeros, and following iterative procedure is performed: a) determining the ghost coefficients by minimizing errors between estimated pixel values and true pixel values calculated over multiple frames; b) updating the estimated pixel values according to the ghost coefficients determined in step a); and if a stopping criterion is satisfied, terminating the iteration procedure; and otherwise, going to step a).

The neighboring locations of the given pixel location may include at least one pixel above, below, left and right of the given pixel location respectively. In another example, the neighboring locations of the given pixel location include eight pixels around the given pixel location with horizontal distance plus vertical distance equal to two. If a derived ghost coefficient has a negative value, the derived ghost coefficient may be set to a non-negative value.

The light energies from the multiple light sources for the given image can be retrieved from data stored during capturing the given image. The images captured may correspond to color images having multiple color components, and where said reducing ghost is performed prior to de-mosaicking the multiple color components. The reducing ghost can be applied to each of the multiple color components separately.

DETAILED DESCRIPTION OF THE INVENTION

Figure 1:
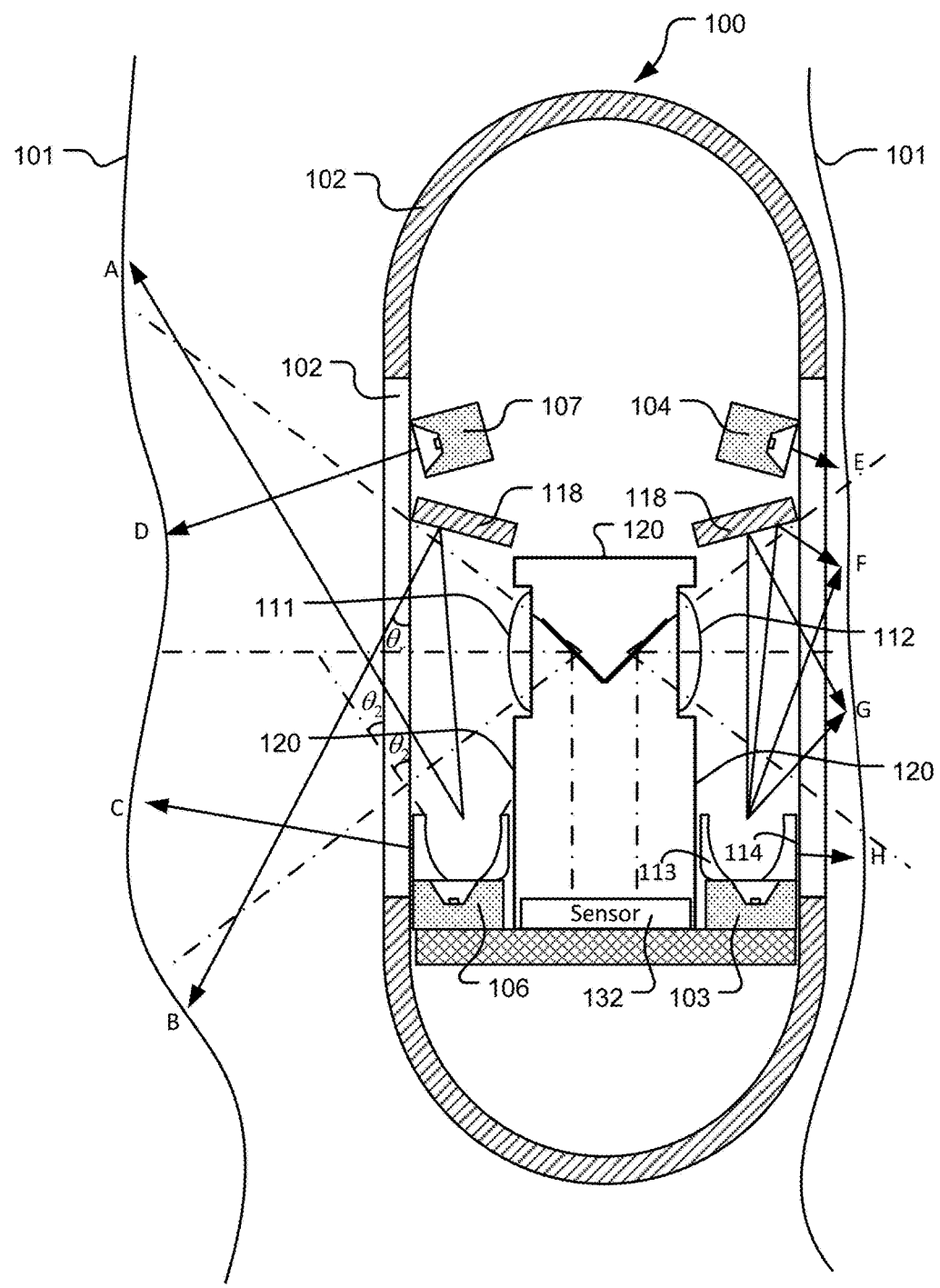
FIG. 1 illustrates an exemplary capsule endoscope using multiple light sources to illuminate the walls of the gastrointestinal (GI) tract, where the reflections of the light sources from the capsule housing cause ghosts in the captured images.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

As mentioned above, a capsule may use multiple electromagnetic radiation sources (e.g. Light Emitting Diode (LEDs)) to illuminate the surface of the organ intended for imaging. For example, the capsule may use eight LEDs arrayed in a ring under the annular truncated CPC 113. The eight LEDs emit out the outer surface 114 of CPC 113 and also through the top of the CPC apertures. The ring LEDs shine upward at an angle to illuminate mucosa close to or touching the capsule. Some of the light from these LEDs is incident upon surfaces within the capsule housing, such as the camera housing 120 and the CPC. These surfaces are designed to minimize scattering and/or to reflect into angles which will not result in ghost. Nevertheless, some scattering occurs. If a mirror image reflected by the housing of the scattering site is within a FOV of one of the objectives (111, 112), a ghost image is created on the sensor 132. On the other hand, the set of sources intended for long-range illumination as disclosed in U.S. Pat. No. 8,636,653 has less issue with the ghosts due to the arrangement whereby the mirror images of any surfaces regions within the capsule illuminated by the long range sources of light are not within the FOV of an objective. Ghosts may also be caused by light directly or indirectly incident on the housing from one or more sources and backscattering from the housing into an objective at a location within the objective's FOV. This backscattering may result from bulk scattering in the housing material, surface roughness or defects, or contamination on the housing surface.

Figure 2:
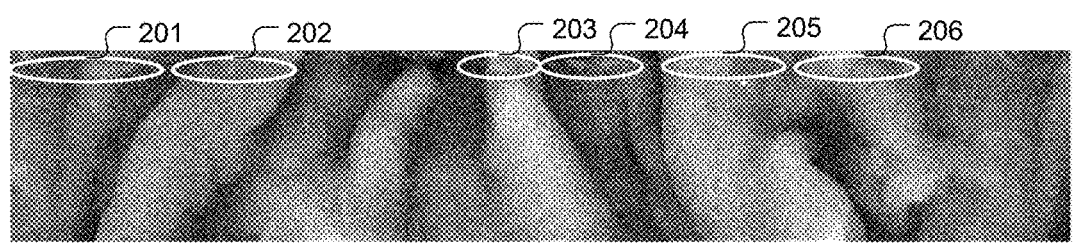
FIG. 2 illustrates an example of a capsule image captured in the small bowel with ghosts, where ghosts manifest streaks of brighter areas in the photo.

While multiple sets of sources may be used in a capsule endoscope, for simplicity, the derivation of ghost parameters in the disclosure hereafter is based on one set of LEDs. However, it is understood that the following derivation of ghost parameters is intended to illustrate the process of ghost parameter derivation and the present invention is not restricted to one single set of electromagnetic radiation sources. FIG. 2 illustrates an example of a capsule image captured in the small bowel with ghosts, where ghosts manifest streaks of brighter areas in the photo. Some of the ghosts are identified by references 201 through 206.

In the following, the process of ghost generation is first formulated. First, each light creates a number of ghost reflections across the capsule images. In other words, each pixel has a ghost value associated with it for every light. This value is called the ghost coefficient $g_{ij}$ for each pixel i and each light j. While a one-dimensional index i is used for the pixel index, it is understood that this one-dimensional index may correspond to two-dimensional pixel coordinates. During the process of capturing images, the light energy of each light may have been optimized to minimize the ghost as described in U.S. Pat. No. 8,636,653. Due to the nature of small ghost signals, many of these coefficients will be near zero, where there are no or little ghost reflections. Furthermore, the light energy of each light applied to each frame can be determined by the capsule endoscope. The light energy of each light applied to each frame can be recorded along with the image data for each frame or recorded separately. The light energy of each light applied to each frame can be retrieved and used for processing associated images.

The captured pixel signal with ghosts is denoted as $P_{iq}^{gh}$. According to present invention, the captured pixel with ghosts is modelled as a sum of the true image data and ghost signals:

$$P_{iq}^{gh} = \Sigma_j g_{ij} L_{jq} + P_{iq} \tag{1}$$

where,
q index for frames,
j index for the light sources,
$P_{iq}$ the true image data, i.e., pixel value without any ghosts for pixel i and frame q,
$L_{jq}$ light energy value for frame q due to light j, and
$g_{ij}$ ghost coefficient for pixel i due to light j.

As shown in eq. (1), the captured pixel $P_{iq}^{gh}$ can be modelled as the sum of the true pixel data $P_{iq}$ and the ghosts, $\Sigma_j g_{ij} L_{jq}$. The task of de-ghosting becomes estimating the true pixel data $P_{iq}$ based on the measured (i.e., captured) pixel data $P_{iq}^{gh}$. In other words, the task of de-ghosting becomes an estimation of the ghosts (i.e., $\Sigma_j g_{ij} L_{jq}$). Once the ghost coefficient $g_{ij}$ is known, the ghost in a captured image can be determined. The ghost can simply be removed by subtracting the ghosts contributed by all light sources, which correspond to the sum of light energy weighted by the ghost coefficients. In order for this to work properly, it is necessary to make sure the pixel values are linear with respect to the light energy by removing any sensor gamma or any other non-linearity in the pixel value associated with the light energy.

The ghosts are relative stable when the capsule endoscope stays in a fixed environment such as the surrounding of the capsule being the air or liquid, and the temperature. When the capsule endoscope travels from an environment surrounded by the air to an environment surrounded by the liquid, the ghosts will be noticeably different. Also, the temperature will play a role on the ghosts. Since the capsule endoscope travels slowing in the gastrointestinal (GI) tract, it is expected that the ghosts are slow varying over a period of time. Since the ghosts are typically slow varying signals, it is possible to utilize multiple captured images over a proper period of time, such as tens or hundreds of images, to determine the underlying ghost coefficients.

Figure 3:
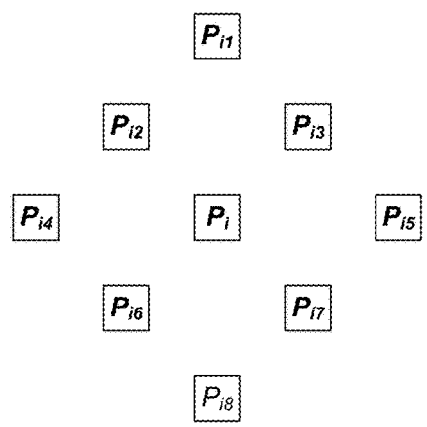
FIG. 3 illustrates an example of surround pixel pattern used to derive the estimated pixel value for the current pixel.

Based on observation of captured images, the ghosts are localized in streaks of narrow areas. Presumably, some surrounding pixels are intact or less affected by ghosts. Therefore, according to one embodiment, the estimate of the actual pixel value is derived based on surrounding neighboring pixels. An example of a surrounding pixel pattern is shown in FIG. 3, where 8 surrounding pixels (i.e., $P_{i1}, \ldots, P_{i8}$) for a current pixel (i.e., $P_i$) may be used to derive the estimated pixel value for the current pixel. Furthermore, the underlying current true pixel may be estimated as the average of the surround pixels minus the ghost values of those pixels calculated so far. Accordingly, the estimated current pixel, $P_{iq}^*$ can be derived as:

$$P_{iq}^* = \frac{1}{N}\Sigma_n(P_{i_nq}^{gh} - \Sigma_j(g_{i_n,j}^* L_{jq})), \quad (2)$$

where $g_{i_n,j}^*$ is the best estimate so far of the ghost coefficients and n is a set of N neighbors of the current pixel. While the estimated current pixel, $P_{iq}^*$ can be derived as the average of neighboring pixels, the estimated current pixel may also be derived as a weighted sum of neighboring pixels:

$$P_{iq}^* = \Sigma_n a_n(P_{i_nq}^{gh} - \Sigma_j(g_{i_n,j}^* L_{jq})), \quad (3)$$

where $a_n$ is the weighting factor and $\Sigma_n a_n = 1$.

In eq. (2) and eq. (3), $g_{i_n,j}^*$ has to be estimated. Since ghosts are slow varying, an embodiment of the present invention uses a sufficiently large number of captured frames to estimate $g_{i_n,j}^*$. For example, the estimation of ghost coefficients can be based on Mean Squared Error (MSE) of the approximation for each pixel i using a large number of captured pictured as defined by:

$$MSE_i = \Sigma_q(P_{iq}^{gh} - P_{iq}^{gh*})^2. \quad (4)$$

In eq. (4), $P_{iq}^{gh*}$ represents the image with ghosts based on the estimated pixel data (i.e., $(P_{iq}^* + \Sigma_j g_{ij} L_{jq})$). Therefore, eq. (4) can be rewritten as:

$$MSE_i = \Sigma_q(P_{iq}^{gh} - \Sigma_j g_{ij} L_{iq} - P_{iq}^*)^2. \quad (5)$$

With a new variable $A_{iq}$ defined as $A_{iq} = P_{iq}^{gh} - P_{iq}^*$, eq. (5) can be rewritten as:

$$MSE_i = \Sigma_q(A_{iq} - \Sigma_j g_{ij} L_{jq})^2 \quad (6).$$

There is an important constraint that the ghost coefficients have to be positive. In other words, spurious light from a light source can only add to the pixel value instead of subtracting from it.

With this constraint, this problem now can be formulated as a well-known problem called non-negative least squares. The solutions to this problem are known in the literature. For example, an online web site provides a short introduction to this problem and also provides some references (https://en.wikipedia.org/wiki/Non-negative least squares).

One way to solve this problem is to take the derivative with respect to the unknowns and set it equal to zero, i.e., $\partial/(\partial g_{ik})(MSE_i)=0$. This gives a sequence of equations (over k) for each pixel i:

$$\Sigma_q A_{iq} L_{kq} = \Sigma_j g_{ij}(\Sigma_q L_{jq} L_{kq}) \quad (7)$$

The term $\Sigma_q L_{jq} L_{kq}$ on the right side of eq. (7) is essentially a square matrix that can be inverted to solve for the ghost coefficients. One way to maintain the non-negative constraint is to remove any of the coefficients that are negative (or less than some threshold) from the set of equations and then do another least squares fit (LSF) on the coefficients that remain. This can be repeated until all coefficients are non-negative, or no coefficients are left and thus there is not a ghost at that pixel.

The steps of the algorithm according to eq. (7) become, for each frame:

1. Calculate the sum of the light energies, $\Sigma_q L_{jq} L_{kq}$.
   Perform this step only once since the light values remain the same.

2. For each pixel, remove ghosts from $P_{iq}^*$ using the previous calculated $g_{i_n,j}^*$ values.
   For the initial iteration, all the ghost coefficients are set to zero so this step is skipped.
   For non-initial iterations, compute $P_{iq}^*$ for each pixel as the average of the neighboring pixels that just had the ghost removed
3. For each pixel, calculate $A_{iq} = P_{iq}^{gh} - P_{iq}^*$
4. Using $A_{iq}$ and the $L_{jq}$ values to calculate all the sums, $\Sigma_q A_{iq} L_{kq}$.

Once all the frames are processed, the process can continue as follows:

5. Solve for the $g_{ij}$ values by inverting the matrix $\Sigma_q A_{iq} L_{kq}$.
6. For any $g_{ij}$ value that is negative or smaller than a threshold:
   Remove them from the list linear equations, and Invert the new matrix
7. Solve for the remain $g_{ij}$ values.
   If any $g_{ij}$ value is negative, go back to step 6
   If all $g_{ij}$ values are zero, there is no ghost at this pixel for this iteration
8. Using the new $g_{ij}$ values go back to the beginning (i.e., step 2) and repeat, unless the pixel values no longer change by a noticeable amount, or the MSE for each pixel is no longer getting smaller by a pre-defined value.

Step 6 of the algorithm describes reducing the number of equations where there are zero or near zero (less than a threshold value) coefficients. Note that in eq. (7), the matrix is only a function of the light values for each frame. Going through each frame once, all the light sum terms ($\Sigma_q L_{iq} L_{kq}$) can be calculated. Since any coefficient can be removed, there can be any combination of linear equations with the presence or absence of a coefficient. For example, if there are 8 light sources then there are $2^8 = 256$ possible sets of linear equations and corresponding matrices. One set is the degenerate set: all coefficients removed and no corresponding matrix is needed. All remaining 255 sets of linear equations and corresponding matrices can be inverted once after the initial sums are generated and saved in memory. This pre-calculation is much more efficient than solving the set of equations over and over again for each pixel.

The MSE in eq. (4), eq. (5) or eq. (6) usually is calculated over a large number of frames, such as hundreds of frames.

Figure 4A:
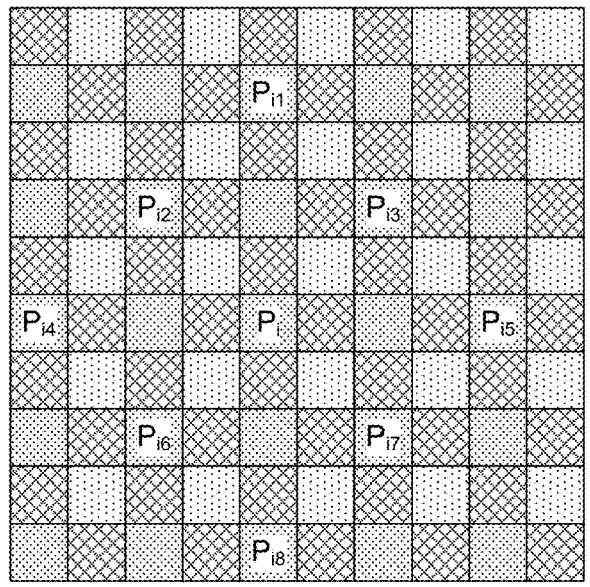
FIG. 4A-FIG. 4C illustrate the neighboring pixel patterns used for deriving the estimated pixels for RGB color planes respectively.
Figure 4B:
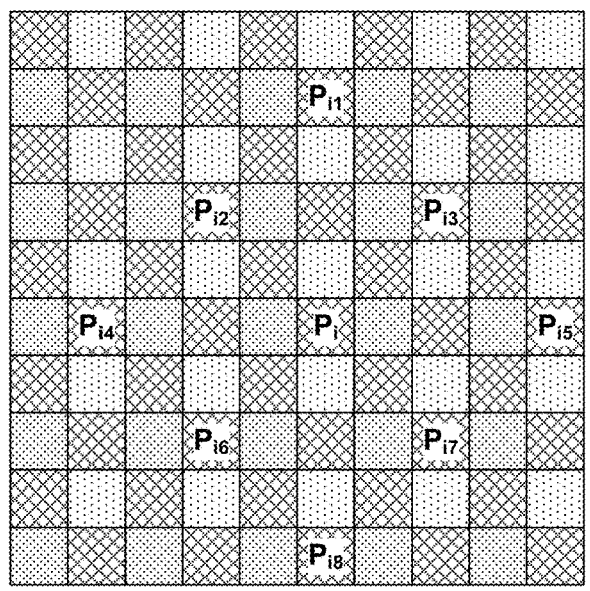
Figure 4C:
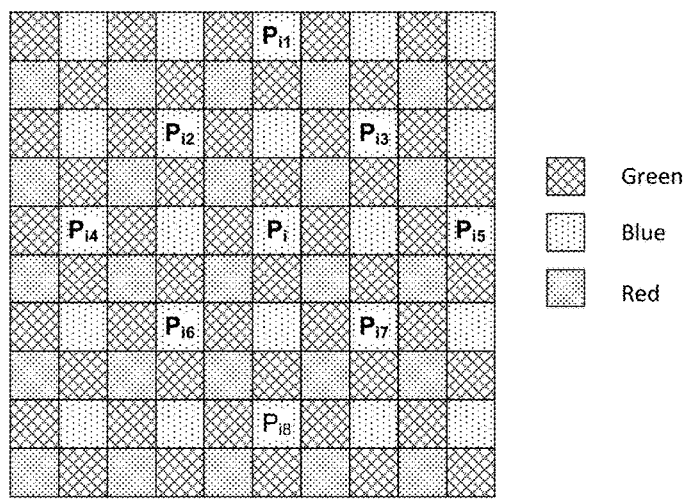

The algorithm described above can be extended to a multicolor image by applying the algorithm to individual color planes independently. For example, the algorithm can be applied to the Bayer pattern from the camera before the RGB data is demosaicked. When applied to each color plane, the estimate is calculated from the neighboring pixels having the same pixel color. For example, the neighboring pixel patterns used for deriving the estimated pixel are shown in FIG. 4A through FIG. 4C for RGB color planes respectively. Again, the pixel patterns for deriving an estimated pixel shall not be construed as limitations of the present invention. Other pixel patterns may also be used as well.

Figure 5:
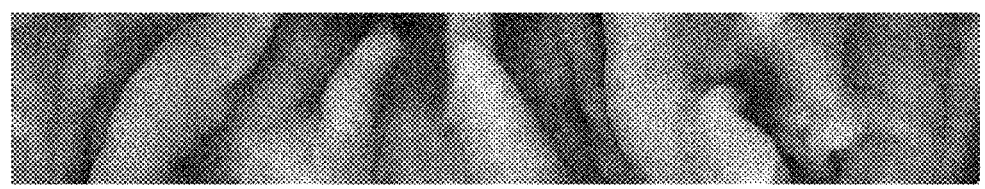
FIG. 5 illustrates a de-ghosted picture for the original picture in FIG. 2 according to an embodiment of the present invention.

FIG. 5 illustrates a de-ghosted picture according to an embodiment of the present invention. Compared to the original picture in FIG. 2, the ghosts are substantially reduced.

Figure 6:
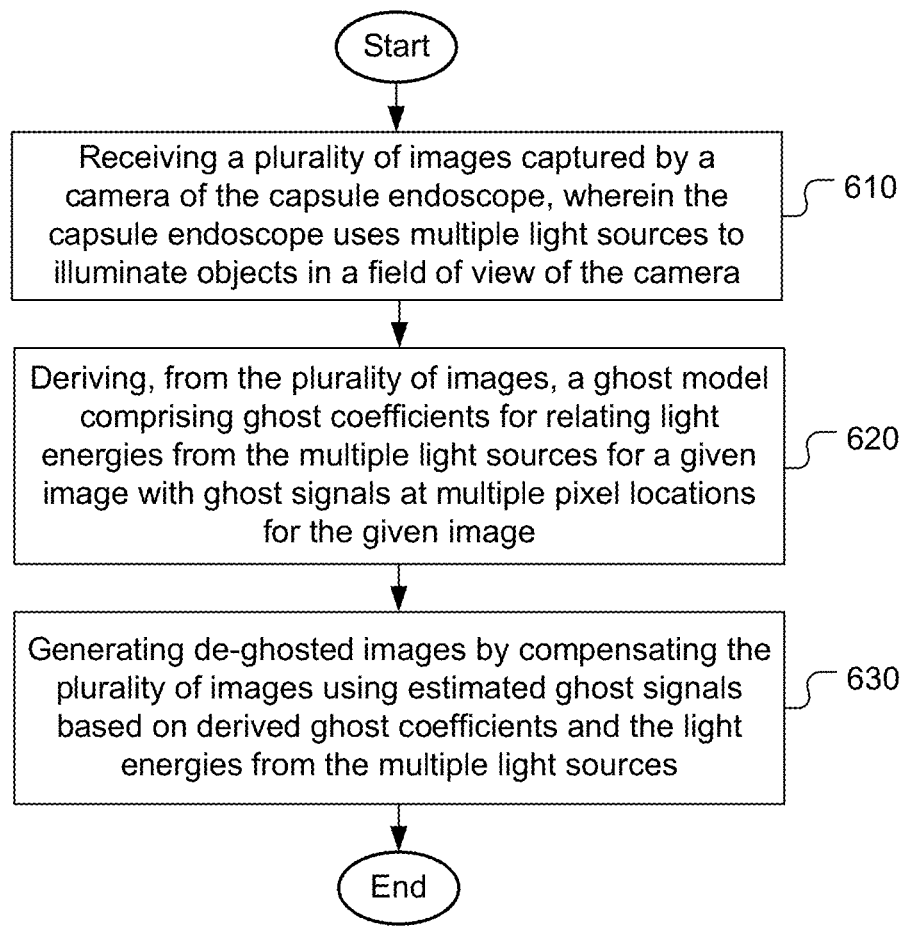
FIG. 6 illustrates a flowchart of an exemplary system for de-ghosting according to an embodiment of the present invention.

FIG. 6 illustrates a flowchart of an exemplary system for de-ghosting according to an embodiment of the present invention. The system receives a plurality of images captured by a camera of the capsule endoscope in step 610, where the capsule endoscope uses multiple light sources to illuminate objects in a field of view of the camera. The plurality of images captured by a camera of the capsule endoscope may be retrieved directly from the capsule endoscope if the capsule endoscope uses on-board storage. The plurality of images captured by a camera of the capsule endoscope may have been previously downloaded and stored in a stand-alone storage device (e.g., flash memory) or a storage device in a system (e.g. hard disk or solid-state hard disk in a workstation, PC or mobile device). In this case, the plurality of images are received or retrieved from such storage device. A ghost model comprising ghost coefficients for relating light energies from the multiple light sources for a given image with ghost signals at multiple pixel locations for the given image is derived from the plurality of images in step 620. As mentioned before, a pre-processing to remove any sensor gamma or any other non-linearity in pixel values of the plurality of images associated with the light energy. De-ghosted images are generated by compensating the plurality of images using estimated ghost signals based on derived ghost coefficients and the light energies from the multiple light sources in step 630.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

Embodiment of the present invention as described above may be implemented in various hardware, software codes, or a combination of both. For example, an embodiment of the present invention can be implemented on a workstation, desktop personal computer (PC), laptop PC, tablet or mobile device, which include one or processor or processors. These processors can be configured to perform particular tasks according to the invention, by executing machine-readable software code or firmware code that defines the particular methods embodied by the invention. The software code or firmware code may be developed in different programming languages and different formats or styles. The software code may also be compiled for different target platforms. However, different code formats, styles and languages of software codes and other means of configuring code to perform the tasks in accordance with the invention will not depart from the spirit and scope of the invention.

The invention may be embodied in other specific forms without departing from its spirit or essential characteristics. The described examples are to be considered in all respects only as illustrative and not restrictive. The scope of the invention is therefore, indicated by the appended claims rather than by the foregoing description. All changes which come within the meaning and range of equivalency of the claims are to be embraced within their scope.

The invention claimed is:

1. A method of reducing ghosts in images captured using a capsule endoscope, wherein captured images contain ghosts caused by reflections off capsule housing of the capsule endoscope by one or more light sources or one or more objects within the capsule endoscope illuminated by said one or more light sources, the method comprising:
   receiving a plurality of images captured by a camera of the capsule endoscope, wherein the capsule endoscope uses one or more light sources to illuminate objects in a field of view of the camera;
   deriving, from the plurality of images, a ghost model comprising ghost coefficients for relating light energies from said one or more light sources for a given image with ghost signals at multiple pixel locations for the given image; and
   generating de-ghosted images by compensating the plurality of images using estimated ghost signals based on derived ghost coefficients and the light energies from said one or more light sources.

2. The method of claim 1, wherein said deriving, from the plurality of images, the ghost model comprises removing any sensor gamma or any other non-linearity in pixel values of the plurality of images associated with the light energy.

3. The method of claim 1, wherein each captured image is modelled as a sum of first pixel values corresponding to true pixel values and ghost signals at respective pixel locations within each picture, and wherein the true pixel value at a given pixel location is estimated by a sum of weighted first pixel values at neighboring locations of the given pixel location to derive an estimated true pixel value.

4. The method of claim 3, wherein the true pixel value at the given pixel location is estimated by an average of the first pixel values at neighboring locations of the given pixel location.

5. The method of claim 3, wherein the ghost coefficients at the given pixel location are estimated by minimizing errors between estimated pixel values and true pixel values calculated over multiple frames.

6. The method of claim 5, wherein the errors between estimated pixel values and true pixel values correspond to mean squared errors.

7. The method of claim 5, wherein the ghost coefficients are allowed to be non-negative only and a non-negative least squares process is used to derive the ghost coefficients.

8. The method of claim 5, wherein the ghost coefficients are initially set to all zeros, and following iterative procedure is performed:
   a) determining the ghost coefficients by minimizing errors between estimated pixel values and true pixel values calculated over multiple frames;
   b) updating the estimated pixel values according to the ghost coefficients determined in step a); and
   c) if a stopping criterion is satisfied, terminating the iteration procedure; and otherwise, going to step a).

9. The method of claim 3, wherein the neighboring locations of the given pixel location include at least one pixel above, below, left and right of the given pixel location respectively.

10. The method of claim 3, wherein the neighboring locations of the given pixel location include eight pixels around the given pixel location with horizontal distance plus vertical distance equal to two.

11. The method of claim 1, wherein if a derived ghost coefficient has a negative value, the derived ghost coefficient is set to a non-negative value.

12. The method of claim 1, wherein the light energies from said one or more light sources for the given image is retrieved from data stored during capturing the given image.

13. The method of claim 1, wherein the images captured correspond to color images having multiple color components, and wherein said reducing ghosts is performed prior to de-mosaicking the multiple color components.

14. The method of claim 13, wherein said reducing ghost is applied to each of the multiple color components separately.

15. An apparatus for reducing ghosts in images captured using a capsule endoscope, wherein captured images contain ghosts caused by reflections off capsule housing of the capsule endoscope by one or more light sources or one or more objects within the capsule endoscope illuminated by said one or more light sources, the apparatus comprising one or more electronic circuits or processors arranged to:

receive a plurality of images captured by a camera of the capsule endoscope, wherein the capsule endoscope uses one or more light sources to illuminate objects in a field of view of the camera;

derive, from the plurality of images, a ghost model comprising ghost coefficients for relating light energies from said one or more light sources for a given image with ghost signals at multiple pixel locations for the given image; and generate de-ghosted images by compensating the plurality of images using estimated ghost signals based on derived ghost coefficients and the light energies from said one or more light sources.

16. The apparatus of claim 15, wherein each captured image is modelled as a sum of first pixel values corresponding to true pixel values and ghost signals at respective pixel locations within each picture, and wherein the true pixel value at a given pixel location is estimated by a sum of weighted first pixel values at neighboring locations of the given pixel location to derive an estimated true pixel value.

17. The apparatus of claim 16, wherein the true pixel value at the given pixel location is estimated by an average of the first pixel values at neighboring locations of the given pixel location.

18. The apparatus of claim 16, wherein the ghost coefficients at the given pixel location are estimated by minimizing errors between estimated pixel values and true pixel values calculated over multiple frames.

* * * * *